United States Patent [19]
Crudele et al.

[11] Patent Number: 6,056,946
[45] Date of Patent: May 2, 2000

[54] HEAT-MEDIATED CONDITIONING FROM LEAVE-ON HAIR CARE COMPOSITIONS CONTAINING SILICONE

[75] Inventors: Joanne Crudele, Chicago; Darshna Bhatt, Schaumburg; Kimberly Kamis, Glenview; Pawel Milczarek, Schaumburg, all of Ill.

[73] Assignee: Helene Curtis, Inc., Chicago, Ill.

[21] Appl. No.: 08/943,609

[22] Filed: Oct. 3, 1997

[51] Int. Cl.[7] .................................................. A61K 7/075
[52] U.S. Cl. .................. 424/70.12; 424/70.1; 424/70.11; 424/70.15; 424/47; 514/944
[58] Field of Search ............................... 424/70.1, 70.11, 424/70.12, 70.15, 47; 514/944

[56] References Cited

U.S. PATENT DOCUMENTS

| | | |
|---|---|---|
| 4,704,272 | 11/1987 | Oh et al. . |
| 4,733,677 | 3/1988 | Gee et al. . |
| 4,741,855 | 5/1988 | Grote et al. . |
| 4,788,006 | 11/1988 | Bolich, Jr. et al. . |
| 5,374,420 | 12/1994 | Gerstein . |

FOREIGN PATENT DOCUMENTS

| | | |
|---|---|---|
| 2098597 | 8/1997 | Australia . |
| 0205306 | 12/1986 | European Pat. Off. . |
| 2745173 | 8/1997 | France . |
| 95/23581A | 3/1988 | WIPO . |

OTHER PUBLICATIONS

STR 8 Product Brochure, Aug. 1996.
International Search Report PCT/EP 98/06242 dated Mar. 4, 1999.

*Primary Examiner*—Jyothsna Venkat
*Attorney, Agent, or Firm*—Matthew Boxer

[57] ABSTRACT

In brief, the present invention is directed to a method for conditioning hair which comprises:
(a) applying to hair a leave-on composition comprising:
  (1) a nonvolatile, silicone conditioning agent;
  (2) a resin; and
  (3) a carrier;
(b) applying heat via a heating appliance to the composition treated hair to dry or style the hair and wherein a reduction in the bending modulus caused by the silicone conditioning agent is at least 1.00%, even when offset by an increase in bending modulus caused by the presence of a resin, and wherein the method of the invention results in the deposition on the hair of at least 30 ug silicone/1 g of hair.

30 Claims, No Drawings

HEAT-MEDIATED CONDITIONING FROM LEAVE-ON HAIR CARE COMPOSITIONS CONTAINING SILICONE

BACKGROUND OF INVENTION AND PRIOR ART

Hair setting is basically the process of shaping wet hair by the steps of stretching and forming the hair during blow drying or by curling the hair, fixing the hair in place after it has been dried and then curling or straightening the hair to give the finishing touches to provide the desired hairstyle.

However, heating the hair often damages the hair. Therefore, it would be highly desirable to develop heat mediated methods for conditioning the hair while styling the hair, which do not result in such damage. It would also be desirable to develop compositions which could be used in such methods.

An inherent problem encountered in hair setting is the natural tendency of the hair to return to its natural shape. For example, the set hair returns to its natural shape almost immediately if moistened or exposed to high humidity.

Investigators have sought to delay the combined action of natural forces and moisture that causes the hair to return to its original state by applying solutions containing naturally-occurring or synthetic polymers after the hair is shaped into a desired configuration. When applied to the shaped hair from aqueous or aqueous/alcoholic solutions (setting lotions), the polymers leave a film on the hair, after drying, to help maintain the hair in the previously shaped configuration. The polymeric film promotes cohesion and gives stability to the hair set. The principal objective of a setting lotion and/or styling aid is to cover the hair with an invisible polymeric film that will give the styled hair a degree of rigidity and protect the hair style against wind and humidity.

The general principles of hair setting are thoroughly discussed by C. Zviak, in The Science of Hair Care, Marcel Dekker, pp. 149–181(1986). Zviak reviews both the polymers used in hair setting products/styling aids and the formulation principles used to produce a hair set product that provides such beneficial hair set properties as improved hairstyle hold, easy application and combing, quick drying and non-stickiness, good hair body and bounce, increased hair volume and gloss, and hydrophobicity. It is evident that in the formulation of any end-use hair-styling product, some of these benefits may be sacrificed to some degree to achieve a competing benefit.

There is sufficient evidence both from both consumer and clinical testing that the use of heat styling appliances is damaging to human hair. For consumers that heat style their hair the primary concern is to use a leave-on product that can protect and improve the condition of their hair while providing preferred setting characteristics.

The claimed invention not only provides good hair setting characteristics and protective benefits, but in addition, uses heat to mediate increased conditioning and softness dependent on the delivery and deposition of conditioning agent between certain known levels.

SUMMARY OF THE INVENTION

The invention is the use of silicone based conditioning agents in leave-on hair care compositions to elicit a heat-mediated reduction in bending modulus, or softening, or conditioning to hair, as compared to air dried, treated hair. The heat required to elicit the effect would be the heat of a blow dryer or styling appliance, ranging from 200° to 400° F. measured at the point of origin of the appliance.

In brief, the present invention is directed to a method for thermal conditioning hair which comprises:
(a) applying to hair a leave-on composition comprising:
   (1) a nonvolatile, silicone conditioning agent;
   (2) a resin; and
   (3) a carrier;
(b) applying heat via a heating appliance to the composition treated hair to dry or style the hair and wherein a reduction in the bending modulus caused by the silicone agent is at least 1.00%, and wherein the method of the invention results in the deposition on the hair of at least 30 ug silicone/1 g of hair.

DETAILED DESCRIPTION OF THE PREFERRED EMBODIMENT

As used herein nonvolatile, silicone conditioning agent means any silicone having a boiling point of 200° C. or greater, typically this would include silicones within a broad range of molecular weight, and having viscosities of between about 5 centistokes to 1 million centistokes.

As used herein % means weight percent unless otherwise indicated.

As used herein hair serum is a silicone hair treatment.

Heat activation is defined as some change that is mediated by use of the composition of the invention with heat, from styling appliances such as a blow dryer, curling iron, hot curlers, hot brush, hot comb, hot rollers, crimper, or hair dryer. From internal testing of various appliances this average temperature can range on the "hot" setting to be 200° to 400° F.

Any nonvolatile, silicone conditioning agent which will deposit silicone on hair may be used in the compositions and methods of the present invention. Silicone agents in the compositions of the present invention include dimethicone, dimethiconol, phenyl trimethicone, dimethicone copolyols, amino functional silicones, organically modified silicone resins such as stearyl siloxysilicate and lauric siloxysilicate, silicone gums, silicone elastomers, and crosslinked siloxane polymers which may be either linear or branched.

Silicone conditioning agents are responsible for a heat-induced reduction in bending modulus or softening of the hair. The preferred non-volatile, silicone conditioning agents are dimethiconol, phenyl trimethicone, and dimethicone copolyol which are added to compositions of the present invention in amounts sufficient to provide good feel and hold characteristics.

Preferred silicones include linear and branched polydimethylsiloxanes, of the following general formula: $(CH_3)_3$ SiO—$[Si(CH_3)_2O]n$—$Si(CH_3)_3$, wherein n is from about 7 to about 15,000, preferably from about 7 to about 9,000. Silicones useful in compositions of the present invention are available from a variety of commercial sources, including General Electric Company and Dow Corning. In addition to the linear and branched polydimethylsiloxanes, the polydimethylsiloxanes can be organically modified to include amine, hydroxyl, alkyl, alkyl aryl, ethoxylated, and propoxylated functionalities.

In accordance with one important embodiment, the composition of the present invention also includes from about 0.001% to about 10%, particularly about 0.01% to about 10%, and preferably from about 0.01% to about 5.0%, by weight of a non-volatile silicone compound or other conditioning agent(s), preferably a water-insoluble, emulsifiable conditioning agent. Any nonvolatile silicone containing agent will work in the present invention provided that the silicone agent deposits sufficient silicone onto the hair.

Using compositions and methods of the invention, wherein the nonvolatile, silicone conditioning agent was present in the compositions at an active range of about 0.1 to about 2.0%, depositing on hair in the range of about 30 ug/g to about 1200 ug/g hair. In these just above mentioned compositions, the nonvolatile, silicone conditioning agents were as follows:

Dimethiconol containing silicone emulsions such as, dimethiconol and dimethiconol/silsesquioxane copolymer (and) sodium C14–16 olefin sulfonate (and) trideceth-12;

Dimethicone copolyol; and

Phenyl Trimethicone.

The resins which can be employed in the compositions and methods of the invention are as follows: A Polyquaternium-11 such as Gafquat 734 of Gafquat 755N; a hydrophilic Polyether Urethane such as Polyurethane Resin 142-89; a Polyquaternium 4 such as Celquat L-200 or Celquat H-100; a Polyvinylpyrrollidine such as PVP K-30; a PVP/Dimethylaminoethyl methacrylate copolymer such as Copolymer 845; a VA/Crotonate/Vinyl Neodecanoate Copolymer such as Resyn 28-2930; an Octylacrylamide/Acrylates/Butylaminoethyl Methacrylate such as Amphomer; and a PVP/VA Copolymer such as PVP/VA E-635.

Other resins include Gantrez 425, 335, and 215 (Ester of PVM/MA Copolymer); Gantrez XL-80 (PVM/MA Decadiene Crosspolymer); LoVocryl (Octylacrylamide/Acrylates/Butlyaminoethyl Methacrylate Copolymer): Luvimer (Acrylates Copolymer); PVP K-60, K-90, K-120 (PVP); PVP/VA 335, 535, 735, 630 (PVP/VA Copolymers); Resyn 28-2913 (VA/Crotonates/Vinyl Neodecanoate Copolymer); and Ultrahold (Acrylate/Acrylamide Copolymer).

Shaping of the hair is best accomplished by first applying the composition to hair while wet, shaping the hair while drying with a heat appliance, and then if needed, physically shaping the hair with a hot styling appliance. The heat softens the resin; thereby, allowing it to spread along the hair shaft. After removing the hot styling appliance, the resin hardens, maintaining the hair in the desired style. In addition, heat interacts with the silicone conditioning agent resulting in reduction in bending modulus; thereby, allowing the hair softer characteristics.

The composition also can include a suspending agent in an amount of about 0.001% to about 10%, by total weight of the composition. The particular suspending agent is not critical and can be selected from any materials known to suspend water-insoluble liquids in leave-on compositions. Suitable suspending agents are for example, distearyl amate (distearyl phthalamic acid); fatty acid alkanolamides; esters of polyols and sugars; polyethyleneglycols; the ethoxylated or propoxylated alkylphenols; ethoxylated or propoxylated fatty alcohols; and the condensation products of ethylene oxide with long chain amides. These suspending agents, as well as numerous others not cited herein, are well known in the art and are fully described in the literature, such as McCUTCHEON'S DETERGENTS AND EMULSIFIERS, 1989 Annual, published by McCutcheon Division, MC Publishing Co.

A nonionic alkanolamide also is optionally included in an amount of about 0.001% to about 5% by weight in the leave-on compositions to provide exceptionally stable emulsification of water-insoluble conditioning agents and to aid in thickening and foam stability.

Suitable alkanolamides include, but are not limited to, those known in the art of hair care formulations, such as cocamide monoethanolamide (MEA), cocamide diethanolamide (DEA), soyamide DEA, lauramide DEA, oleamide monoisopropylamide (MIPA), stearamide MEA, myristamide MEA, lauramide MEA, capramide DEA, ricinoleamide DEA, myristamide DEA, stearamide DEA, oleylamide DEA, tallowamide DEA, lauramide MIPA, tallowamide MEA, isostearamide DEA, isostearamide MEA and combinations thereof. Other suitable suspending agents are disclosed in Oh et al. U.S. Pat. No. 4,704,272 Grote et al. U.S. Pat. No. 4,741,855; and Bolich, Jr. et al. U.S. Pat. No. 4,788,006, which patents are hereby incorporated by reference.

Other useful suspending and thickening agents can be used instead of the alkanolamides such as sodium alginate; guar gum; xanthan gum; gum arabic; cellulose derivatives, such as carbomer, methylcellulose, hydroxybutylcellulose, hydroxyethylcellulose, hydroxypropylcellulose and carboxymethylcellulose; and various synthetic polymeric thickeners, such as the polyacrylic acid derivatives.

Emulsion stabilizers also may be used in compositions of the invention. Useful examples include, such compounds as polyethylene glycol, silicone copolyols, polyvinyl alcohol, sorbitan monostearate, oleth-2, sorbitan monolaurate, and nonionic block copolymers of ethylene oxide and propylene oxide such as those marketed by BASF Wyandotte under the name PLURONICS(r). When present, such stabilizers comprise from about 0.05% to about 1%, preferably from about 0.1% to about 0.8%, by weight of the composition.

The propellant gas included in the aerosol forms of the compositions of the present invention can be any liquefiable gas conventionally used for aerosol containers. Examples of materials that are suitable for use as propellants are trichlorofluoromethane, hydrofluorocarbon, dichlorodifluoromethane, dichlorotetrafluoroethane, monochlorodifluoromethane, trichlorotrifluoroethane, dimethyl ether, propane, n-butane and isobutane, used singly or admixed. Water-soluble gases such as dimethyl ether, carbon dioxide, and/or nitrous oxide also can be used to obtain aerosols having reduced flammability. Water-immiscible, liquified, hydrocarbon and halogenated hydrocarbon gases such as propane, butane, hydrofluorocarbon, and chlorofluorocarbons can be used advantageously to deliver the contents of the aerosol container without the dramatic pressure drops associated with other immiscible gases. Here there is no concern for the head space to be left inside the aerosol container, because the liquified gas will sit on top of the aqueous formulation and the pressure inside the container is always the vapor pressure of saturated hydrocarbon vapor. Other insoluble, compressed gases such as nitrogen, helium and fully-fluorinated oxetanes and oxepanes also are useful to deliver the compositions from aerosol containers.

Other means of delivery of the above-described leave-on, styling aid compositions include, pump sprayers, all forms of bag-in-can devices, in situ carbon dioxide generator systems, compressors, and the like. The amount of the propellant gas is governed by normal factors well known in the aerosol art. For mousses, the level of propellant is generally from about 3% to about 30%, preferably from about 5% to about 15% of the total composition. For hairsprays, the level of propellant is generally from about 10% to about 40%, preferably from about 15% to about 35% of the total composition. If a propellant such as dimethyl ether utilizes a vapor pressure suppressant (e.g., trichlorethane or dichloromethane), for weight percentage calculations, the amount of suppressant is included as part of the propellant.

Other common cosmetic additives can be incorporated with the essential ingredients of the present invention, as long as the basic properties of the composition are not adversely affected. These additives include, but are not limited to, commonly used fragrances, dyes, opacifiers, pearlescing agents, foam stabilizers, preservatives, water softening agents, acids, bases, sequestering agents, buffers, proteins, amino acids, and the like; and will usually be present in weight percentages of less than about 1% each, and about 2% to about 5% in total.

The composition vehicle, or carrier, is predominantly water or organic solvents which can be added to the composition in order to solubilize compounds that are not sufficiently soluble in water. Suitable solvents include the lower alcohols like most preferred ethanol and isopropanol; polyols like glycerol; glycols or glycol ethers, like 2-butoxyethanol, ethylene glycol, ethylene glycol monoethyl ether, propylene glycol and diethylene glycol monomethyl ether; and mixtures thereof. These solvents can be present in the composition of the present invention in an amount from about 1% to about 95% by weight.

The compositions can be thickened, for example, with sodium alginate, gum arabic, cellulose derivatives such as carbomer, methylcellulose, hydroxyethylcellulose, hydroxypropylmethylcellulose and carboxylmethyl-cellulose, and various polymeric thickeners, such as acrylic acid derivatives. It is also possible to use inorganic thickeners such as bentonite. These thickeners are preferably present in the amount from about 0.1% to about 10% by weight and, in particular, from about 0.5% to about 3% by weight, relative to the total weight of the composition.

The compositions also can include anionic, amphoteric or nonionic surfactants. Representative nonionic surfactants include polyols and sugars; the polyethoxylated and/or polypropoxylated alkylphenols; the polyhydroxylated polyethers of fatty alcohols; and the condensation products of ethylene oxide with long chain mercaptans or long chain amides. Similarly, representative anionic surfactants include alkali metal salts, ammonium salts or salts of amines or amino alcohols of fatty acids such as oleic acid; of the sulfates of fatty alcohols, principally $C_{12}$–$C_{14}$ and $C_{16}$ fatty alcohols; of the sulfates of polyethoxylated fatty alcohols; the alkylbenzenesulfonates, such as those wherein the alkyl moiety has about 12 to about 22 carbon atoms; or the alkylarylpolyether sulfates and monoglyceride sulfates. All these nonionic and anionic surfactants, as well as numerous others not cited here, are well known in the art and are fully described in the literature.

The optional alcohols employed in the compositions of the invention are an aliphatic straight or branched chain monohydric alcohol having 2 to about 4 carbon atoms. Isopropanol and especially ethanol are preferred. The concentration of the alcohol in the composition can be 0–95%, as low as 0%, preferably 0–80%, more preferably 0–75%.

FORMULATION EXAMPLES

As shown in the data below, silicone conditioning agents, contained within the formulations of the invention and depositing silicone within certain ranges, are responsible for the heat-mediated reduction in bending modulus, or hair softening, or conditioning. These formulations listed in Table I are made by methods known in the art.

TABLE I

Leave-On Composition Formulas

| FORMULA INGREDIENTS | WEIGHT % | BENDING MODULUS RESULT |
|---|---|---|
| Formula A: Mousse | | |
| water, deionized | q.s.* | Approximate Reduction of 28.00% |
| polyquaternium 11 | 8.09600000 | |
| dimethiconol, dimethiconol/silsesquioxane copolymer | 1.84000000 | |
| preservative | 0.09936000 | |
| SD alcohol 40-B (190 proof) | 7.63600000 | |
| nonoxynol-9 | 0.49680000 | |
| fragrance | 0.13800000 | |
| butane or isobutane | 8.00000000 | |
| phytantriol | 0.025 | |

| FORMULA B INGREDIENTS | WEIGHT % | BENDING MODULUS RESULT |
|---|---|---|
| Formula B: Leave-On Conditioner | | |
| water, soft | q.s.* | Approximate Reduction of 16.00% |
| dl-panthenol | 0.8000000 | |
| PEG-2 oleammonium chloride & propylene glycol | 1.0000000 | |
| cetrimonium chloride | 1.5000000 | |
| propylene glycol, USP | 0.5000000 | |
| preservative | 0.3000000 | |
| nonoxynol-10 | 0.2500000 | |
| fragrance | 0.3000000 | |
| phytantriol | 0.0250000 | |
| sodium dihydrogen phosphate, granular | 0.2000000 | |
| phosphoric acid, 85% | 0.0500000 | |
| dimethicone, silica | 0.0100000 | |

| FORMULA C INGREDIENTS | WEIGHT % | BENDING MODULUS RESULT |
|---|---|---|
| Formula C: Non-Aerosol Hair Spray | | |
| SD alcohol 40-B (190 proof) | 81.5487000 | Approximate Reduction of 40.00% |
| aminomethyl propanol | 0.5770000 | |
| octylacrylamide/acrylates/butylaminoethyl methacrylate | 3.0000000 | |
| PVP/VA copolymer | 1.0000000 | |
| dimethicone copolyol | 0.1000000 | |
| fragrance | 0.3000000 | |
| phytantriol | 0.0250000 | |
| water, soft | q.s.* | |

| FORMULA D INGREDIENTS | WEIGHT % | BENDING MODULUS RESULT |
|---|---|---|
| Formula D: Aerosol Hair Spray | | |
| SD alcohol 40-B (200 proof) | q.s. | Approximate Reduction of 13.00%. |
| aminomethyl propanol | 0.5062500 | |
| octylacrylamide/acrylates/butylaminoethyl methacrylate | 2.2500000 | |
| dimethicone copolyol | 0.0750000 | |
| VA/crotonates/vinyl neodecanoate copolymer | 1.5000000 | |
| phenyl trimethicone | 0.2625000 | |
| PPG-12-PEG-50-lanolin | 0.1875000 | |
| fragrance | 0.2625000 | |
| hydrofluorocarbon 152-A, butane | 25.0000000 | |
| phytantiol | 0.025 | |

*q.s.-quantity sufficient for total weight % to be equal to 100%.

TESTING METHODS
Dynamic Mechanical Testing of Bending Modulus

Dynamic mechanical testing of the force or modulus to bend a bundle of hair fibers characterizes the stiffness of the hair array, i.e., its resistance to a controlled normal force imposed on the array in the vertical direction. If the modulus increases with treatment the array is stiffer. If the modulus decreases with treatment the array is less stiff; softer; fibers have reduced interfiber friction.

The measurement of bending modulus is not unique to analysis of the physical properties of hair, but reported works had been exclusively devoted to the properties of single hair fiber (see Robbins, Clarence R., Chemical and Physical Behavior of Hair, Third edition. Springer-Verlag, New York. 1993 herein incorporated by reference) and therefore never addressed the characteristics of multiple fibers. In addition, the bending modulus was calculated from the deflection of a single fiber in a static not dynamic mode as used in this test method and reported in the literature for other materials (Lee, T. H., Boey, F. Y., and Loh, N. L. Characterization of Fibre-Reinforced PPS Composite By Dynamic Mechanical Analysis: Effect of Aspect Ratio and Static Stress. *Composites Science and Technology* 49 (1993) 217–223.)

Instruments are commercially available to measure the mechanical properties of a variety of materials, hair included. The Perkin Elmer DMA 7 Dynamic Mechanical Analyzer, used at Helene Curtis R&D, is equipped to perform three point bending modulus, and was used for thermal studies of bending modulus of treated hair. The use of a hair bundle or array allows evaluation of multiple fiber changes and/or fiber interaction in contrast to single fiber effect.

Two hundred fifty fibers of the same length are selected from a regular brown hair tress. The fibers are wetted and aligned on a flat surface to form a ribbon-like swatch. Single drop of water proof adhesive is placed at five spots on the swatch. The distance between each junction is about 1 inch. When dry, four bundles are cut from one swatch.

Eight hair bundles are treated with composition per treatment group. The weight of each hair bundle is measured prior to the test in order to assure that the amount of composition applied remains at a constant proportion to the mass of hair of 1:10 for shampoos and 3:5 with respect to conditioners. For rinse-off products such as shampoos and conditioners, the desired amount of product is applied with a micropipette to the wet hair, worked in for 30 seconds and rinsed out in warm water for 30 seconds. All samples are air dried in the instrument at 72° F. and a controlled humidity of 30%. To heat the sample in the testing chamber the DMA furnace is engaged to 200° F., and the sample is heated for approximately 7 minutes.

The results of testing are presented in Table I with the formulas. Hair arrays treated with the formulations of the invention: mousse, leave-on conditioner, aerosol and nonaerosol hair sprays exhibit a statistically significant reduction in bending modulus following heat treatment. Measurement of the storage bending modulus of untreated, air dried hair vs. heated hair reveals that untreated hair will exhibit an increase in bending modulus of approximately +8.00%, probably due to water loss. Hair arrays treated with a mousse formulated without silicone exhibit nearly the exact opposite change in modulus (24.00% increase) compared to the same mousse formulated with silicone (formula A in Table I) which produced a 28.00% reduction in modulus with heat. All decreases in bending modulus listed in Table I are statistically significant at >95% confidence level using a t-test to compare the means.

What is claimed is:

1. A method for thermal conditioning and softening hair which comprises:
    (a) applying to hair a leave-on composition comprising:
        (1) a non-volatile, silicone conditioning agent;
        (2) a resin; and
        (3) a carrier;
    (b) applying heat via a heating appliance to the composition treated hair to dry or style the hair and wherein a reduction in the bending modulus caused by the silicone styling agent is at least 1.00%.

2. A method according to claim 1, wherein the silicone conditioning agent is non-volatile having a boiling point greater than 200° C., and having viscosities ranging from about 5 centistokes to about 1 million centistokes.

3. A method according to claim 1, wherein the nonvolatile, silicone conditioning agent is selected from the group consisting of linear and branched polydimethylsiloxanes, of the following formula: (CH3)3SiO(Si(CH3)2O)nSiCH3)3n wherein n is from about 7 to about 15,000; and further comprising polydimethylsiloxanes which are organically modified to include amine, hydroxyl, alkyl, alkylaryl, ethoxylated and propoxylated functionalities.

4. A method according to claim 1, wherein the nonvolatile, silicone conditioning agent is selected from the group consisting of:
    Dimethiconol and Dimethiconol/Silsesquioxane Copolymer and Sodium C14–16 Olefin Sulfonate;
    Dimethicone Copolyol; and
    Phenyl Trimethicone.

5. A method according to claim 1, wherein the nonvolatile, silicone conditioning agent is in an emulsion.

6. A method according to claim 1, wherein the nonvolatile, silicone conditioning agent is a defoamer.

7. A method according to claim 1, wherein the composition is a mousse, nonaerosol spray, aerosol spray, leave-on conditioner, gel, leave-on lotion, or hair serum.

8. A method according to claim 1, wherein the styling resin is selected from the group consisting of: A Polyquaternium-11; a hydrophilic Polyether Urethane; a Polyquaternium-4; a Polyvinylpyrrollidine; a PVP/Dimethylaminoethyl methacrylate copolymer; a VA/Crotonate/Vinyl Neodecanoate Copolymer; an Octylacrylamide/Acrylates/Butylaminoethyl Methacrylate; and a PVP/VA Copolymer.

9. A method according to claim 1, wherein the heating appliance is a blow-dryer, curling iron, hot comb, hot brush, hot curlers, hot rollers, crimper, or hair dryer.

10. A method according to claim 1, wherein the temperature of the heating appliance during the heating step is from about 200° F. to about 400° F. from point of origin of the appliance.

11. A method according to claim 1, wherein the composition is a hair serum.

12. A method according to claim 1, wherein the hair being styled has an ornament in it.

13. A method according to claim 1, wherein the hair being styled is in a hairpiece, extension, or wig.

14. A method for thermal conditioning and softening hair which comprises:
    (a) applying to hair a leave-on composition comprising:
        (1) a non-volatile silicone conditioning agent;
        (2) a resin; and
        (3) a carrier;
    (b) applying heat via a heating appliance to the composition treated hair to dry or style the hair wherein the method of the invention results in the deposition on the hair of at least 30 ug silicone/1 g of hair.

15. A method according to claim 14, wherein the silicone conditioning agent is non-volatile, having a boiling point greater than 200° C., and having viscosities ranging from about 5 centistokes to about 1 million centistokes.

16. A method according to claim 14, wherein the nonvolatile, silicone conditioning agent is selected from the group consisting of linear and branched polydimethylsiloxanes, of the following formula: $(CH_3)_3SiO(Si(CH_3)_2O)_nSiCH_3)_{3n}$ wherein n is from about 7 to about 15,000; and further comprising polydimethylsiloxanes which are organically modified to include amine, hydroxyl, alkyl, alkylaryl, ethoxylated and propoxylated functionalities.

17. A method according to claim 14, wherein the silicone conditioning agent is in an emulsion.

18. A method according to claim 1, wherein the nonvolatile, silicone conditioning agent is a defoamer.

19. A method according to claim 14, wherein the composition is a mousse, nonaerosol spray, aerosol spray, leave-on conditioner, gel, leave-on lotion or hair serum.

20. A method according to claim 14, wherein the styling resin is selected from the group consisting of: A Polyquaternium-11; a hydrophilic Polyether Urethane; a Polyquaternium-4; a Polyvinylpyrrollidine; a PVP/Dimethylaminoethyl methacrylate copolymer; a VA/Crotonate/Vinyl Neodecanoate Copolymer; an Octylacrylamide/Acrylates/Butylaminoethyl Methacrylate; and a PVP/VA Copolymer.

21. A method according to claim 14, wherein the heating appliance is a blow-dryer, curling iron, hot comb, hot brush, hot curlers, hot rollers, crimper, or hair dryer.

22. A method according to claim 14, wherein temperature of the heating appliance during the heating step is from about 200° F. to about 400° F. at point of origin of the appliance.

23. A method according to claim 14, wherein the composition is a hair serum.

24. A method according to claim 14, wherein the hair being styled has an ornament in it.

25. A method according to claim 14, wherein the hair being styled is in a hairpiece, extension, or wig.

26. A method for thermal conditioning of hair which comprises:
    (a) applying to hair a leave-on composition comprising:
        (1) a nonvolatile, silicone conditioning agent;
        (2) a styling resin and
        (3) a carrier;
    (b) applying heat via a heating appliance to the composition treated hair to dry or style the hair and wherein a reduction in the bending modulus caused by the silicone styling agent is at least 1.00%, even when offset by an increase in bending modulus caused by the presence of a styling resin, and wherein the method of the invention results in the deposition on the hair of at least 30 ug silicone/1 g of hair.

27. A method for thermal conditioning hair according to claim 1 wherein the reduction in the bending modulus caused by the silicone agent is at least 13.00%–40.00%.

28. A method for thermal conditioning hair according to claim 1 wherein the amount of silicone deposited on the hair is at least 30 ug silicone/1 g of hair.

29. A method for thermal conditioning and softening of hair which comprises:
    (a) applying to hair a leave-on composition comprising:
        (1) a nonvolatile, silicone conditioning agent;
        (2) a carrier;
    (b) applying heat via a heating appliance to the composition treated hair to dry or style the hair and wherein a reduction in the bending modulus caused by the silicone conditioning agent is at least 1.00%, even when offset by an increase in bending modulus caused by the presence of a styling resin, and wherein the method of the invention results in the deposition on the hair of at least 30 ug silicone/1 g of hair.

30. A method according to claim 29, wherein the leave-on composition is a leave-on conditioner spray.

* * * * *